United States Patent

Ban et al.

[11] Patent Number: 6,034,283
[45] Date of Patent: Mar. 7, 2000

[54] PROCESS FOR PRODUCTION OF CYCLIC ALCOHOLS

[75] Inventors: Masakazu Ban; Mineyuki Iwasaki, both of Kurashiki, Japan

[73] Assignee: Asahi Kasei Kogyo Kabushiki Kaisha, Osaka, Japan

[21] Appl. No.: 09/111,890

[22] Filed: Jul. 8, 1998

[30] Foreign Application Priority Data

Jul. 18, 1997 [JP] Japan ..................................... 9-208347

[51] Int. Cl.[7] ................................................... C07C 29/20
[52] U.S. Cl. ..................... 568/835; 715/716; 715/821; 715/838; 715/839; 715/895; 715/896; 715/898; 715/897; 502/60; 502/61; 502/63; 502/64
[58] Field of Search ..................................... 568/835, 715, 568/716, 821, 838, 839, 895, 896, 897, 898; 502/60, 61, 63, 64

[56] References Cited

U.S. PATENT DOCUMENTS 4,499,313  2/1985  Okumura et al. ......................... 568/897
5,405,814  4/1995  Beech, Jr. et al. ......................... 502/53
5,508,244  4/1996  Watanabe et al. ......................... 502/64

*Primary Examiner*—Joseph McKane
*Attorney, Agent, or Firm*—Pennie & Edmonds LLP

[57] ABSTRACT

A process for producing a cyclic alcohol by a catalytic hydration reaction of a starting cyclic olefin represented by the following formula (1) and water:

$$C_sH_{2s-2-t}R_t \qquad (1)$$

wherein R is a hydrogen atom, an alkyl group having 1 to 4 carbon atoms, a phenyl group or a cyclohexyl group; s is an integer of 5 to 12; and t is an integer of 1 to 4, which comprises supplying a part or the whole of a residue left after separation of said cyclic alcohol from an oil phase containing said cyclic alcohol, unreacted cyclic olefin and impurities having a boiling point between the boiling point of said starting cyclic olefin and that of said cyclic alcohol to a distillation column (s), and recycling the unreacted cyclic olefin obtained after removal of said impurities.

8 Claims, 1 Drawing Sheet

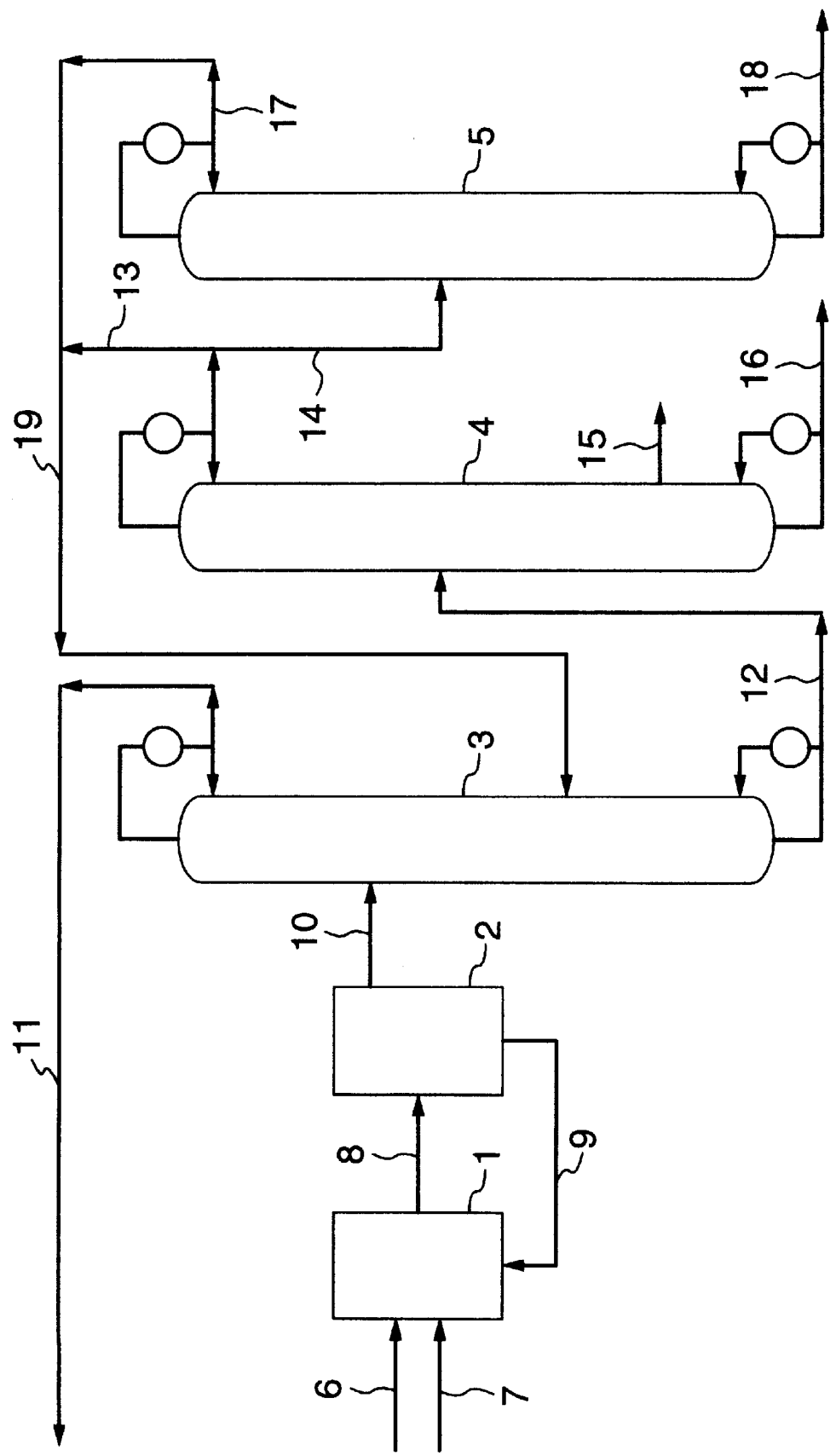

PROCESS FOR PRODUCTION OF CYCLIC ALCOHOLS

BACKGROUND OF THE INVENTION

1. Field of the Invention

The present invention relates to a process for producing cyclic alcohols by a catalytic hydration reaction of cyclic olefins in the presence of an oil phase containing a cyclic olefin, an aqueous phase and a catalyst, wherein the unreacted cyclic olefin is recycled.

2. Description of the Related Art

Production of cyclic alcohols by using a crystalline metallosilicate as a solid catalyst in the hydration reaction of cyclic olefins is discussed in many literatures and patents. For instance, JP-B-2-31056 proposes a method for producing cyclic alcohols by hydrating cyclic olefins using as catalyst a crystalline aluminosilicate having a primary particle size of not greater than 0.5 μm. This publication teaches that in case a crystalline aluminosilicate having a primary particle size of not greater than 0.5 μm is used as catalyst, there are formed two phases, i.e. an oil phase and an aqueous phase, in the reaction solution, with the crystalline aluminosilicate present in the aqueous phase, when the cyclic olefin to water weight ratio is in the range of 0.001 to 100. It also states that the cyclic alcohol produced from this reaction mostly exists in the oil phase, and the cyclic olefin and cyclic alcohol mixture obtained from the oil phase can be easily separated to obtain a cyclic alcohol because of large difference in boiling point. There is shown as a typical example of production method a process which comprises drawing out part of the two-phase reaction solution continuously, allowing it to stand to cause layer separation, taking out the oil phase from the upper layer, and yielding a cyclic alcohol from this oil phase by distillation or other means, while recovering and recycling the unreacted cyclic olefin.

It is known that in the production of cyclic alcohols by the hydration of cyclic olefins, trace amounts of the isomeride of the cyclic olefin and the hydrate thereof are formed as byproducts (See, for instance, JP-A-60-104028). JP-A-4-41448 notes that the presence of trace amounts of these byproducts in the cyclic olefin and cyclic alcohol mixture withdrawn from the hydration reactor poses a serious problem when the cyclic alcohol is separated in a distillation column and the residue is recycled continuously as the starting material for the hydration reaction. Specifically, said cyclic olefin and its isomeride, and said cyclic alcohol and the hydrate of its isomeride are all close to 1 in relative volatility, so that when their mixture is separated in a distillation column, the hydrate of the cyclic olefin isomeride stays as an impurity in the cyclic alcohol while the isomeride of the cyclic olefin remains in the residue, which is recycled as the starting material for the hydration reaction. Therefore, as such operations are continued, the cyclic olefin isomeride is accumulated in the starting material for the hydration reaction, and also the hydrate of such cyclic olefin isomeride in the reaction-product increases, causing excessive reduction of purity of the produced cyclic alcohol. So, in JP-A-4-41448, in order to obtain a high-purity cyclic alcohol, it is proposed to control the concentration of the cyclic olefin isomeride in the residue recycled as the starting material for the hydration reaction. According to this method, the purity of the produced cyclic alcohol is claimed to be 99.73 wt % after 20 hours of the reaction in Example 1.

According to the knowledge of the present inventors, however, it was found that when the above reaction is carried out industrially for a long time, there takes place a reduction of purity of the produced cyclic alcohol even if the isomeride of the cyclic olefin and its hydrate are removed sufficiently, although this was not called to account in the above-mentioned JP-A-4-41448 because of the short operation time.

An object of the present invention is to provide a process for producing cyclic alcohols through distillation, which process enables continues long-time operation and is capable of producing a prescribed amount of high-purity cyclic alcohol, with its impurity concentration sharply reduced, i.e. in a high yield.

As a result of extensive studies for solving the above problems, the present inventors found for the first time that the cause of the reduction of purity of the reaction product cyclic alcohol resides in the impurities having a boiling point between the boiling point of the cyclic olefin and that of the cyclic alcohol, which has not been called in question in the short-time catalytic hydration reactions. Said impurities are accumulated continuously in the mixed oil phase composed of the unreacted cyclic olefin and cyclic alcohol. They are small in amount in the initial stage of the reaction, but they are concentrated with time to an unignorable level. Increase of the accumulation of said impurities causes a corresponding increase of the inclusion of the impurities in the purified cyclic alcohol. Said impurities in the mixed oil phase are recycled along with the unreacted cyclic olefin from a part above the liquid feed part of the distillation column to the reactor, but since the yield of the cyclic alcohol depends on the amount of the cyclic olefin supplied to the reactor, and the like, the increase of the concentration of said impurities, namely the decrease of the concentration of the unreacted cyclic olefin recycled to the reactor, gives rise to the problem that the yield of the cyclic alcohol is reduced unless the operating conditions are changed. As means for increasing the purity of the purified cyclic alcohol, a method is known in which the heat duty of the reboiler used in distillation separation is elevated to remove said impurities in the cyclic alcohol. This method, however, involves the problem to cause an increase of heat duty itself, and is also incapable of reducing the amount of the impurities in the recycled cyclic olefin.

Further researches by the present inventors have led to the disclosure of the fact that in the process for yielding a cyclic alcohol, when the distillation residue separated from the cyclic alcohol is supplied to another distillation column for removing the impurities having a boiling point between the boiling point of the cyclic olefin and that of the cyclic alcohol so that the unreacted cyclic olefin cleared of said impurities will be recycled, it becomes possible to run the operation continuously for a long time, the concentration of the impurities is remarkably reduced without increasing the heat duty applied to the distillation column, and a high-purity cyclic alcohol can be obtained without reducing the production and yield of the cyclic alcohol. The present invention has been completed on the basis of the above finding.

SUMMARY OF THE INVENTION

Thus, the present invention consists in:

1) A process for producing a cyclic alcohol by a catalytic hydration reaction of a starting cyclic olefin represented by the following formula (1) and water:

$$C_sH_{2s-2-t}R_t \tag{1}$$

(wherein R is a hydrogen atom, an alkyl group having 1 to 4 carbon atoms, a phenyl group or a cyclohexyl group; s is an integer of 5 to 12; and t is an integer of 1 to 4), which-comprises supplying a part or the whole of a residue left after separation of said cyclic alcohol from an oil phase containing said cyclic alcohol, unreacted cyclic olefin and impurities having a boiling point between the boiling point of said starting cyclic olefin and that of said cyclic alcohol to a distillation column(s), and recycling the unreacted cyclic olefin obtained after removal of said impurities;

2) A process for producing a cyclic alcohol set forth in 1) above, wherein the cyclic alcohol is distilled by using 1 to m distillation columns (m being an integer of 1 to 5) and separated from a product discharge part of the mth distillation column, and the residue is continuously or intermittently drawn out from a part above the product discharge part of the mth distillation column or from any pertinent part of any one of the first to (m−1)th distillation columns and supplied to another distillation column;

3) A process for producing a cyclic alcohol set forth in 1) or 2) above, wherein the concentration of the impurities in the cyclic olefin at the inlet of the catalytic hydration reactor is 5% by weight or less;

4) A process for producing a cyclic alcohol set forth in any one of 1) to 3) above, wherein the catalytic hydration reaction is carried out in the presence of a crystalline metallosilicate containing at least one metal selected from the group consisting of aluminum, boron, gallium, titanium, chromium, iron, zinc, phosphorus, vanadium and copper, said-metallosilicate being used as catalyst;

5) A process for producing a cyclic alcohol set forth in 4) above, wherein the catalyst is a crystalline metallosilicate represented by the formula (2):

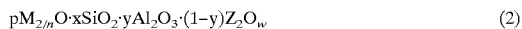

$$pM_{2/n}O \cdot xSiO_2 \cdot yAl_2O_3 \cdot (1-y)Z_2O_w \quad (2)$$

wherein M is at least one n-valent cation, O is oxygen, Si is silicon, Al is aluminum, Z is at least one w-valent metal other than M and aluminum, selected from the group consisting of boron, gallium, titanium, chromium, iron, zinc, phosphorus, vanadium and copper; n is an integer of 1 to 6, w is an integer of 1 to 6, and $0.3 \leq p \leq 1.5$, $1 \leq x \leq 1,000$ and $0 \leq y \leq 1$;

6) A process for producing a cyclic alcohol set forth in 4) or 5) above, wherein the crystalline metallosilicate is the one having a primary particle size of 0.5 μm or less;

7) A process for producing a cyclic alcohol set forth in any one of 4) to 6) above, wherein the crystalline metallosilicate is a crystalline aluminosilicate ZSM-5;

8) A process for producing a cyclic alcohol set forth in any one of 1) to 7) above, wherein the cyclic alcohol is cyclohexanol; and 9) A process for producing a cyclic alcohol set forth in any one of 1) to 8) above, wherein the impurities contain toluene, norcamphane, methylcyclohexane, xylene, n-heptane, ethylbenzene or styrene.

According to the cyclic alcohol production process of the present invention, it is possible to run the continuous operation for a long time and to obtain high-purity cyclic alcohols with a sharply decreased impurity concentration, at a constant rate and in a high yield without increasing the heat duty exerted to the distillation columns. In this respect, the present invention is of very high industrial value.

BRIEF DESCRIPTION OF THE DRAWING

FIG. 1 illustrates a process sheet for carrying out the present invention.

PREFERRED EMBODIMENTS OF THE INVENTION

The invention will be explained while referring to FIG. 1 as required.

The catalyst used in the present invention is a crystalline metallosilicate, preferably the one containing at least one metal selected from the group consisting of aluminum, born, gallium, titanium, chromium, iron, zinc, phosphorus, vanadium and copper. A typical example of such crystalline metallosilicates is the one represented by the above-shown formula (2) which indicates the composition expressed in terms of molar ratios of the anhydride oxides.

In the formula (2), M is a cation, in the crystalline metallosilicate, preferably proton or a cation of a metal of the Group IB, IIA, IIB, IIIA, IIIB, IVB, VB, VIB, VIIB or VIII of the Periodic Table, more preferably proton. Z is at least one metal other than M and aluminum, which metal is selected from the group consisting of boron, gallium, titanium, chromium, iron, zinc, phosphorus, vanadium and copper. These metals are taken up in the crystals during hydrothermal synthesis of the crystalline metallosilicate and do not come out from the metallosilicate even in the subsequent ion exchange operation. Of these metals, boron, gallium, titanium, chromium and iron are particularly preferred.

The crystalline metallosilicate used in the present invention is the one having a primary particle size of preferably not greater than 0.5 μm, more preferably not greater than 0.1 μm, further preferably not greater than 0.05 μm. The lower limit of the particle size is defined by the expression "crystallinity". A crystal is a structure in which the atoms are arranged regularly and periodically according to a certain symmetry, and whereby the diffraction of the X-rays occurs (see Encyclopaedia Chimica, Vol. 3, p. 349, "Crystals", Kyoritsu Shuppan, 1963). Therefore, where a certain period occurs and the diffraction of the X-rays is observed, there exists a certain finite dimention based on the crystal structure. Hence, it can be said that the crystalline metallosilicate used in the present invention is preferably the one in which the diffraction of the X-rays occurs and which has a primary particle size of not greater than 0.5 μm.

The shape and size of such primary particles are diversified, but in the present invention, the particles are called "primary particles" or to have "primary particle size" when the diameter of the smallest width portion of each particle as observed under a scanning electron microscope is measured and those particles having diameters equal to or less than the thus measured value account for 50% in number or more of the whole particles. In this case, if the primary particle size is 0.5 μm or less, it is possible to use the secondary particles formed by agglomeration of the primary particles, and the like even though the size of such secondary particles has been enlarged.

Further, in some cases, it may be found difficult to distinguish between unevenness on the surfaces of a large particle and agglomeration of the primary particles, from scanning electron micrographs. In such a case, the "fine particle" is defined to be a particle in which the ratio of acid points on the external surface (hereinafter referred to as external surface acid points) to the total acid points calculated as H type is 0.03 or more, preferably 0.05 or more, more preferably 0.1 or more.

The determination of the ratio of the external surface acid points to the total acid points is explained below.

Before measuring the acid points, the crystalline metallosilicate used in the present invention needs to be converted into H type. There are available various methods for converting a crystalline metallosilicate into H type, and the method varies depending on whether or not an organic material is used in the synthesizing system and on the type of the organic material when it is used. Hereupon the conversion into H type is carried out as follows: The slurry used in the present invention is filtered and then washed with 5 times as much amount of water as the slurry. In case an organic material is used in the synthesizing system, the obtained cakes are dried at 120° C. for 8 hours, then calcined at 500° C. for 6 hours in a stream of air to remove the organic material, and added to 1N nitric acid to form a 10 wt % slurry, and after conducting ion exchange at 60° C. for 4 hours, the slurry is filtered, washed with 5 times as much amount of water as the slurry, and dried at 120° C. for 10 hours to produce an H type crystalline metallosilicate.

In case no organic material is used in the synthesizing system, the cakes obtained after filtration followed by washing with water are directly added to 1N nitric acid, after which the same process as described above is followed.

The acid points of the thus obtained H type crystalline metallosilicate are determined by the following method (CATALYST, Vol. 25, p. 461 (1983)).

A gas chromatograph GC-7A and a data processor CR-1A, both mfd. by Shimadzu Corp., were used for the determination of the acid points. The sample (0.2–1 g) is packed in a SUS short column having an inner diameter of 4 mm and a total length of 80 mm, and the column is secured to the sample side flow passage in a thermostat of said gas chromatograph. Helium gas is passed through the column at a flow rate of 50 ml/min as carrier gas, and the temperature of the thermostat is set at 325° C.

Next, a determined amount (0.2–2 ml) of an amine (pyridine or 4-methylquinoline) is injected intermittently into the inlet port of the sample side flow passage at intervals of a predetermined period (2–5 minutes) by using a microsyringe. The carrier gas which has passed through the packed column is analyzed by using a FID type detector, obtaining a chromatogram showing the change of amine concentration with time, with the peaks emerging periodically.

The amine adsorption on the sample approaches saturation as the number of times of injection increases, and this accordingly increases the amount of non-adsorbed amine. Therefore, in the above chromatograph, the peak area (Si) corresponding to the second injection of amine approaches the area (So) corresponding to the amount of amine injected.

The amine adsorption Ao ($\mu$mol/g) per unit weight of the sample can be determined from the following equation (a):

$$Ao = \frac{1}{W}\sum_{i=1}^{x}\left(1 - \frac{Si}{So}\right)do \tag{a}$$

wherein W is a sample weight(g) and do is the amount of one injection of amine ($\mu$mol).

In the present invention, the amine injection is repeated k times until the Si to So ratio became Si/So $\geq$ 0.98, and the amine adsorption A($\mu$mol/g) was calculated from the following equation (b):

$$A = \frac{1}{W}\sum_{i=1}^{k}\left(1 - \frac{Si}{So}\right)do \tag{b}$$

Wherein W is a sample weight (g) and do is the amount of one injection of amine ($\mu$mol).

The "total acid points" in the present invention are represented by the pyridine adsorption when pyridine is used as amine in the determination, and the "external surface acid points" are represented by the 4-methylquinoline adsorption when 4-methylquinoline is used as amine in the determination. Therefore, the ratio of the external surface acid points to the total acid points is given by 4-methylquinoline adsorption/pyridine adsorption.

Examples of the crystalline metallosilicate catalysts usable in the present invention include mordenite, faujasite, clinoptilolite, L-type zeolite, chabazite, erionite, ferrierite, crystalline aluminosilicates such as ZSM zeolite developed by Mobil Oil Co., crystalline aluminometallosilicates also containing metals other than aluminum, such as boron, gallium, titanium, chromium, iron, zinc, phosphorus, vanadium and copper, and metallosilicates substantially free of aluminum, such as gallosilicate and borosilicate.

It is also possible to use AZ-1 (JP-A-59-128210), TPZ-3 (JP-A-58-110419), Nu-3 (JP-A-57-3714), Nu-5 (JP-A-57-129820), Nu-6 (JP-A-57-123817) and Nu-10 (JP-A-57-200218).

Usually, the hydration reactions of cyclic olefins are accompanied by a side reaction such as isomerization or polymerization. In a hydration reaction of cyclohexene, for example, byproducts such as methylcyclopentenes, dicyclohexyl ether and bicyclohexyl are formed. For suppressing such side reactions to enable the high-yield production of cyclic alcohols, it is expedient to use as catalyst, for example, a crystalline aluminosilicate ZSM-5 disclosed in JP-B-4-41131. ZSM-5 is a zeolite developed by Mobil Oil Co. (see U.S. Pat. No. 3,702,886), which has the three-dimensional pores having the inlets of the 10-membered oxygen-containing rings in the crystal structure in which the silica to alumina molar ratio is 20 or more.

As the cyclic olefin used in the catalytic hydration reaction according to the present invention, there can be used the compounds represented by the formula (1), which include, for example, cyclopentene, cyclohexene, cycloheptene, cyclooctene, cyclononene, cyclodecene, cycloundecene, cyclododecene, methylcyclohexene, dimethylcyclohexene, trimethylcyclohexene, tetramethylcyclohexene, phenylcyclohexene and the like, and mixtures thereof. These cyclic olefins are hydrated to form the corresponding cyclic alcohols.

The impurities in the present invention are the compounds which have a boiling point between the boiling point of the cyclic olefins represented by the formula (1) and the boiling point of the cyclic alcohol produced from a catalytic hydration reaction of a cyclic olefin with water. In case the cyclic olefin is cyclohexene, such impurity compounds include toluene, norcamphane, methylcyclohexane, xylene, n-heptane, ethylbenzene, styrene and the like. The concentration of the impurities contained in the cyclic olefin used as starting material in the present invention is not specified, but usually it falls within the range not less than 1 ppm by weight and less than 1,000 ppm by weight. These impurities are present in the cyclic aromatic compounds used as starting material for said cyclic olefins. It is considered that as they get into the hydration reaction system in an unreacted form, they are eventually mixed in the cyclic olefins.

As for the reaction temperature, a low temperature is advantageous in view of the equilibrium of the olefin hydration reaction and the suppression of the side reactions, but too a low reaction temperature results in a reduced yield because of the low reaction rate. The preferred range of reaction temperature, therefore, is from 50° C. to 300° C.

Regarding the pressure under which the reaction is conducted, although the reaction can be carried out either under reduced pressure or under pressure, it is imperative to apply a pressure under which both of the reactants cyclic olefin and water can maintain the liquid phase.

For the reaction of the present invention, the cyclic olefin/water molar ratio can be selected from a wide range, but it should be noted that the excessively high proportion of the cyclic olefin leads to a reduction of the conversion of cyclic olefin. On the other hand, if the proportion of water is excessively high, although the conversion of cyclic olefin can be elevated, there are not only a disadvantage in the aspect of the separation and purification of the produced cyclic alcohol but also a necessity for enlarging the capacity of the reactor and the liquid/liquid separator used in the subsequent step. Such enlargement of capacity of the operating devices, however, are inadvisable from the viewpoints of manufacture, maintenance and operation of such devices.

In the present invention, therefore, the molar ratio of the cyclic olefin to water is preferably within the range from 0.01 to 100. As for the cyclic olefin/catalyst weight ratio, although such ratio is variable depending on the reaction conditions such as temperature, pressure and cyclic olefin/water molar ratio in the continuous reaction, it is usually desirable that the weight ratio of the catalyst to the cyclic olefin supplied to the reactor in one hour is in the range from 0.005 to 100.

The oil phase taken out from the liquid/liquid separator after the catalytic hydration reaction in the present invention is a solution containing a cyclic alcohol, a cyclic olefin, the impurities accompanying the cyclic olefin including the impurities concerned in the present invention, the high-boiling matter formed as byproduct in a trace amount during the hydration reaction, and a trace amount of catalyst. The cyclic alcohol concentration in the oil phase extracted from the separator is around 12% by weight. For obtaining a cyclic alcohol as an industrial product, generally the cyclic alcohol produced from the reaction is concentrated and purified by pertinent operations such as distillation while the unreacted cyclic olefin is recovered and recycled, with the impurities such as high-boiling byproducts and catalyst being separated away.

The present invention is characterized in that the residue obtained after separating the cyclic alcohol by a suitable means such as distillation, said residue containing the unreacted cyclic olefin and the impurities concerned in the present invention, is supplied into a distillation column(s) for removing said impurities, and then recycled. The residue containing the unreacted cyclic olefin and the impurities concerned in the present invention may be the one from which the cyclic alcohol has been completely or partly removed.

For example, in case one to m columns are used for distillation and the cyclic alcohol obtained from a catalytic hydration reaction of a cyclic olefin is distilled and drawn out from a product discharge part set at a part higher than the mth distillation column bottom but lower than the solution feed part, the oil drawn out from a portion above the product discharge part of the mth column or the oil drawn out from a pertinent part of any one of the 1st to (m−1)th column corresponds to said residue from which the impurities are to be removed. It is most desirable that the oil withdrawn from a section where the impurity concentration is highest in the said region be treated as the object from which the impurities are to be removed.

The residue supplied to the another distillation column(s) for removing the impurities is recycled after the impurities have been removed from the bottom of the column by distillation. The distillation column(s) used for removing the impurities are operated so that the impurity concentration in the oil drawn out from the column top will become 0 to less than 5% by weight.

The oil drawn out from the top of the distillation column used for the impurity removal may be recycled to any of the 1st to mth distillation columns or to the reactor, or may be distributed to both of them, depending on the concentration of the cyclic alcohol contained in said oil.

The amount of the residue to be supplied to the distillation column(s) used for the removal of impurities and the column operation conditions are properly selected so that the impurity concentration at the inlet of the reactor will be maintained 0 to less than 5% by weight, preferably 0 to less than 1% by weight, more preferably 0 to less than 1,000 ppm by weight. By maintaining the impurity concentration at the reactor inlet in the above range, it is possible to obtain a desired amount of a cyclic alcohol with an impurity concentration of less than 0.1% by weight, preferably less than 100 ppm by weight, more preferably less than 10 ppm by weight.

The present invention is further explained with reference to the following Examples, but the present invention is not to be limited by these Examples in any way.

The crystalline metallosilicate content of the cyclic alcohol and cyclic olefin solution was determined by filtering said solution, washing the filtration residue, drying it at 120° C. for one hour, further calcining it at 500° C. for 4 hours, measuring the weight of the resultant solid, and calculating therefrom the content of said subject material.

EXAMPLE 1

Fine particles of a crystalline aluminosilicate ZSM-5 disclosed in JP-A-3-193622 were used as the catalyst in the hydration-reaction. The primary particle size of this crystalline aluminosilicate was 0.1 $\mu$m.

Said crystalline aluminosilicate was mixed with water twice the quantity of said aluminosilicate in weight ratio to form a catalyst slurry, and the hydration reaction was carried out at 125° C. by pressurizing the gaseous phase section to 6 kg/cm$^2$G with nitrogen gas with stirring at a stirrer speed of 530 rpm, supplying cyclohexene through a feed pipe 6 in FIG. 1 at a rate of one part by weight per one part by weight of the catalyst per hour, while also supplying water through another feed pipe 7 in an amount corresponding to the water consumption in the reaction.

The amount of the catalyst slurry returned to the reactor 1 via a return pipe 9 was adjusted so that the oil/water interfacial level in a separator 2 will be positioned below the discharge pipe 10.

The solution supplied to the distillation column 3 via the discharge pipe 10 was a cyclohexene mixed solution containing 11.8 wt % of cyclohexanol, 18 ppm by weight of crystalline aluminosilicate, 0.20 wt % of toluene, 0.27 wt % of norcamphane, and 0.23 wt % of methylcyclohexane.

100 parts by weight of the produced solution was supplied to the distillation column 3 via the discharge pipe 10. 88.198 parts by weight of the distillate was drawn out from the top of the column 3 and recycled to the reactor 1 via the discharge pipe 11 and feed pipe 6. The composition of this distillate was 99.21 wt % cyclohexene, 0.23 wt % toluene, 0.30 wt % norcamphane and 0.26 wt % methylcyclohexane. The bottom solution of the column 3 was supplied to the column 4 via a discharge pipe 12. From the bottom of the column 4, 0.500 part by weight of the catalyst and cyclohexanole were discharged out of the system via a discharge pipe 16. From the top of the column 4, 0.044 part by weight of the distillate was taken out and supplied to another distillation column 5 for separation of impurities via a discharge pipe 14, with the rest of the distillate being recycled to the column 3 via the discharge pipe 13 and recycle pipe 19. This distillate had the composition of 91.50 wt % cyclohexene, 1.80 wt % toluene, 2.50 wt % norcamphane, 2.10 wt % methylcyclohexane and 2.10 wt % cyclohexanol. From the bottom of the column 5, 0.0040 part by weight of a cyclohexene mixed solution comprising 19.20 wt % of toluene, 26.60 wt % of norcamphane, 22.40 wt % of methylcyclohexane and 22.40 wt % of cyclohexanol was discharged out of the system, and from the top of this column, 0.0400 part by weight of a cyclohexene mixed solution containing 3 ppm weight of methylcyclohexane was recycled to the column 3 via the discharge pipe 17 and recycle pipe 19. When this round of operation was run continuously, the impurity concentration at the inlet of the reactor 1 was 530 ppm by weight, and there could be obtained 11.298 parts by weight of cyclohexanol containing 2 ppm by weight of cyclohexene and 5 ppm by weight of toluene as vapor from a product discharge pipe 15 provided at a part higher than the discharge pipe 16 but lower than the joint &f the discharge pipe 12 to the column 4.

The heat duty of the reboilers of the columns 3, 4 and 5 was 717 kcal/kg-product in total.

Example 1 shows the result of 720 hours after the start of the hydration reaction, but even after such a long period as 1,440 hours of operation, there was observed no increase of impurities (cyclohexene: 2 ppm by weight; toluene: 5 ppm by weight, in cyclohexanol) nor was seen any significant increase of heat duty of the reboilers (716 kcal/kg-product). The results are shown in Table 1.

EXAMPLE 2

The same procedure as in Example 1 was conducted except that a crystalline gallosilicate described in Example 1 of JP-A-8-245454 was used as catalyst. The solution supplied to the distillation column 3 via the discharge pipe 10 was a cyclohexene mixed solution comprising 8.40 wt % of cyclohexanol, 25 ppm by weight of crystalline gallosilicate, 0.18 wt % of toluene, 0.24 wt % of norcamphane and 0.21 wt % of methylcyclohexane. 100 parts by weight of the produced solution was supplied to the column 3 via the discharge pipe 10. 91.598 parts by weight of the distillate was taken out from the top of the column 3 and recylced to the reactor 1 via the discharge pipe 11 and the material feed pipe 6. This distillate had the composition of 99.31 wt % cyclohexene, 0.20 wt % toluene, 0.26 wt % norcamphane and 0.23 wt % methylcyclohexane. 0.500 part by weight of the catalyst and cyclohexanol were taken out from the bottom of the column 4 and discharged out of the system via the discharge pipe 16. 0.037 part by weight of the distillate was supplied from the top of the column 4 to the column 5 via the discharge pipe 14 for removing the impurities. The rest of the distillate was recycled to the column 3 via the discharge pipe 13 and recycle pipe 19. This portion of the distillate had the composition of 92.80 wt % cyclohexene, 1.63 wt % toluene, 2.21 wt % norcamphane, 1.85 wt % methylcyclohexane and 1.51 wt % cyclohexanol. 0.0030 part by weight of a cyclohexene mixed solution containing 20.30 wt % of toluene, 27.50 wt % of norcamphane, 23.00 wt % of methylcyclohexane and 18.80 wt % of cyclohexanol was taken out from the bottom of the column 5 and discharged out of the system via the discharge pipe 18, while 0.0340 part by weight of a cyclohexene mixed solution containing 2 ppm by weight of methylcyclohexane was taken out from the top of the column 5 and recycled to the column 3 via the discharge pipe 17 and the recycle pipe 19. When the above operation was run continuously, 7.899 parts by weight of cyclohexanol containing 3 ppm by weight of cyclohexne and 4 ppm by weight of toluene was obtained as vapor from the product discharge pipe 15 provided at a position higher than the discharge pipe 16 but lower than the joint of the discharge pipe 12 to the column 4. The heat duty of the reboilers of the columns 3, 4 and 5 was 695 kcal/kg-product in total.

Example 2 shows the results of 720 hours after the start of the hydration reaction, but even after such a long period as 1,440 hours of operation, there was seen no increase of impurities in the product cyclohexanol, with cyclohexene being 3 ppm by weight and toluene being 4 ppm by weight, nor was noted a significant increase of heat duty of the reboilers, which was 694 kcal/kg-product. The cyclohexanol production was 7.90 parts by weight, indicating no decrease of the yield. The results are shown in Table 1.

Comparative Example 1

The same procedure as in Example 1 was carried out except for the omission of the impurity removal in the column 5. 720 hours after the start of the reaction, the solution supplied to the column 3 via the discharge pipe 10 was a cyclohexene mixed solution containing 11.38 wt % of cyclohexanol, 18 ppm by weight of crystalline aluminosilicate, 1.12 wt % of toluene, 1.65 wt % of norcamphane and 1.43 wt % of methylcyclohexane.

As in Example 1, 100 parts by weight of this product solution was supplied to the distillation column 3 via the discharge pipe 10. 0.50 part by weight of the catalyst and cyclohexanol were taken out from the bottom of the column 4 and discharged out of the system via the discharge pipe 16. The distillate (88.87 parts by weight) from the top of the column 3 had the composition of 94.99 wt % cyclohexene, 0.28 wt % cyclohexanol, 1.26 wt % toluene, 1.86 wt % norcamphane and 1.61 wt % methylcyclohexane.

There was noted a change in the amounts of the impurities in the cyclohexanol. Although cyclohexene was the same (2 ppm by weight) as in Example 1, toluene increased to 12 ppm by weight, norcamphane to 10 ppm by weight and methylcyclohexane to 5 ppm by weight, respectively.

Also, the heat duty of the reboilers in the columns 3 and 4 increased to 729 kcal/kg-product in total, while the cyclohexanole obtained from the product discharge pipe 15 decreased to 10.63 parts by weight.

Regarding the impurities in cyclohexanol of 1,440 hours after the start of the hydration reaction, although cyclohexene remained unchanged at 2 ppm by weight, toluene increased to 19 ppm by weight, norcamphane to 21 ppm by weight and methylcyclohexane to 12 ppm by weight, respectively.

The heat duty of the reboilers in the columns 3 and 4 increased to 737 kcal/kg-product in total, while the cyclohexanol obtained from the product discharge pipe 15 dropped to 10.29 parts by weight. The results are shown in Table 1.

Comparative Example 2

The same procedure as in Example 2 was conducted except for the omission of the impurity removal in the column 5. 720 hours after the start of the reaction, the solution supplied to the column 3 via the discharge pipe 10 was a cyclohexene mixed solution containing 8.21 wt % of cyclohexanol, 25 ppm by weight of crystalline gallosilicate, 0.78 wt % of toluene, 1.15 wt % of norcamphane and 1.00 wt % of methylcyclohexane.

As in Example 2, 100 parts by weight of this product solution was supplied to the column 3 via the discharge pipe 10, and 0.50 part by weight of the catalyst and cyclohexanol were drawn out from the bottom of the column 4 and discharged out of the system via the discharge pipe 16. The distillate (91.97 parts by weight) from the top of the column 3 had the composition of 88.86 wt % cyclohexene, 0.18 wt % cyclohexanol, 0.78 wt % toluene, 1.15 wt % norcamphane and 1.00 wt % methylcyclohexane.

Regarding the impurities in cyclohexanole, although cyclohexene remained unchanged at 3 ppm by weight, toluene increased to 11 ppm by weight, norcamphane to 8 ppm by weight and methylcyclohexane to 3 ppm by weight, respectively.

The heat duty of the reboilers in the columns 3 and 4 increased to 701 kcal/kg-product in total, and cyclohexanol obtained from the product discharge pipe 15 decreased to 7.53 parts by weight.

1,440 hours after the start of the reaction, cyclohexene in cyclohexanol remained unchanged at 3 ppm by weight but toluene increased to 18 ppm by weight, norcamphane to 19 ppm by weight and methylcyclohexane to 6 ppm by weight, respectively, the heat duty of the columns 3 and 4 increased to 709 kcal/kg-product in total, and the yield of cyclohexanol from the product discharge pipe 15 decreased to 7.39 parts by weight. The results are shown in Table 1.

TABLE 1

| | Run time elapsed (hr) | Total reboiler heat duty (kcal/ kg-product) | Toluene content-ration in produced cyclohexanol (ppm by weight) | Amount of cyclohexanol produced (part by weight) |
|---|---|---|---|---|
| Example 1 | 720 | 717 | 5 | 11.298 |
| | 1440 | 716 | 5 | 11.300 |
| Comp. Example 1 | 720 | 729 | 12 | 10.630 |
| | 1440 | 737 | 19 | 10.290 |
| Example 2 | 720 | 695 | 4 | 7.899 |
| | 1440 | 694 | 4 | 7.900 |
| Comp. Example 2 | 720 | 701 | 11 | 7.530 |
| | 1440 | 709 | 18 | 7.390 |

What is claimed is:

1. A process for producing a cyclic alcohol by a catalytic hydration reaction of a starting cyclic olefin represented by the following formula (1) and water:

$$C_sH_{2s-2-t}R_t \quad (1)$$

wherein R is a hydrogen atom, an alkyl group having 1 to 4 carbon atoms, a phenyl group or a cyclohexyl group; s is an integer of 5 to 12; and t is an integer of 1 to 4, which comprises supplying a part or the whole of a residue left after separation of said cyclic alcohol from an oil phase containing said cyclic alcohol, unreacted cyclic olefin and impurities having a boiling point between the boiling point of said starting cyclic olefin and that of said cyclic alcohol to a distillation column (s), and recycling the unreacted cyclic olefin obtained after removal of said impurities, wherein the concentration of the impurities in the cyclic olefin at the inlet of the catalytic hydration reactor is 5% by weight or less.

2. The process according to claim 1, wherein the cyclic alcohol is distilled by using 1 to m distillation columns, wherein m is an integer of 1 to 5, and separated from a product discharge part of the mth distillation column, and the residue is continuously or intermittently drawn out from a part above the product discharge part of the mth distillation column or from any pertinent part of any one of the first to (m−1)th distillation column(s) and supplied to another distillation column.

3. The process according to claim 1, wherein the catalytic hydration reaction is carried out in the presence of a crystalline metallosilicate containing at least one metal selected from the group consisting of aluminum, boron, gallium, titanium, chromium, iron, zinc, phosphorus, vanadium and copper, said metallosilicate being used as catalyst.

4. The process according to claim 3, wherein the catalyst is a crystalline metallosilicate represented by the formula (2):

$$pM_{2/n}O \cdot xSiO_2 \cdot yAl_2O_3 \cdot (1-y)Z_2O_W \quad (2)$$

wherein M is at least one n-valent cation; O is oxygen; Si is silicon; Al is aluminum; Z is at least one w-valent metal other than M and aluminum, selected from the group consisting of boron, gallium, titanium, chromium, iron, zinc, phosphorus, vanadium and copper; n is an integer of 1 to 6; w is an integer of 1 to 6; and $0.3 \leq p \leq 1.5$; $1 \leq x \leq 1,000$; and $0 \leq y \leq 1$.

5. The process according to claim 3, wherein the crystalline metallosilicate is the one having a primary particle size of 0.5 μm or less.

6. The process according to claim 3, wherein the crystalline metallosilicate is a crystalline aluminosilicate ZSM-5.

7. The process according to claim 1, wherein the cyclic alcohol is cyclohexanol.

8. The process according to claim 1, wherein the impurities contain toluene, norcamphane, methylcyclohexane, xylene, n-heptane, ethylbenzene or styrene.

* * * * *